United States Patent
Zimmermann et al.

(10) Patent No.: US 12,128,626 B2
(45) Date of Patent: Oct. 29, 2024

(54) METHOD FOR PRODUCING THREE-DIMENSIONAL HYDROGEL STRUCTURES AND DEVICE FOR THE LAYERWISE BUILDING-UP OF SUCH HYDROGEL STRUCTURES

(71) Applicant: Fraunhofer-Gesellschaft zur Foerderung der angewandten Forschung e. V., Munich (DE)

(72) Inventors: Heiko Zimmermann, Sulzbach (DE); Julia Neubauer, Wuerzburg (DE); Michael Gepp, Sulzbach (DE); Benjamin Fischer, Wuerzburg (DE)

(73) Assignee: Fraunhofer-Gesellschaft zur Foerderung der angewandten Forschung e. V., Munich (DE)

( * ) Notice: Subject to any disclaimer, the term of this patent is extended or adjusted under 35 U.S.C. 154(b) by 565 days.

(21) Appl. No.: 17/263,455

(22) PCT Filed: Aug. 28, 2019

(86) PCT No.: PCT/EP2019/072999
§ 371 (c)(1),
(2) Date: Jan. 26, 2021

(87) PCT Pub. No.: WO2020/052981
PCT Pub. Date: Mar. 19, 2020

(65) Prior Publication Data
US 2021/0283847 A1   Sep. 16, 2021

(30) Foreign Application Priority Data
Sep. 14, 2018   (EP) .................................. 18194428

(51) Int. Cl.
*B29C 64/364*   (2017.01)
*A61L 27/18*   (2006.01)
(Continued)

(52) U.S. Cl.
CPC ............ *B29C 64/364* (2017.08); *A61L 27/18* (2013.01); *A61L 27/20* (2013.01); *A61L 27/22* (2013.01);
(Continued)

(58) Field of Classification Search
CPC ... B29C 64/106; B29C 64/112; B29C 64/118; B29C 64/124; B29C 64/129;
(Continued)

(56) References Cited

U.S. PATENT DOCUMENTS 10,265,911 B1 *   4/2019   Capri ............... G05B 19/41875
2008/0020049 A1   1/2008   Darling et al.
(Continued)

FOREIGN PATENT DOCUMENTS

CN   1820791 A   8/2006
CN   107041971 A   8/2017
(Continued)

OTHER PUBLICATIONS

Extended European Search Report for Application No. 18194428.1 dated Apr. 18, 2019.
(Continued)

*Primary Examiner* — Jamel M Nelson
(74) *Attorney, Agent, or Firm* — CAESAR RIVISE, PC (57) ABSTRACT

The invention relates to a method for producing three-dimensional, preferably porous, hydrogel structures by means of layer build-up technique, wherein the method comprises the following steps. Providing (S1) of a liquid hydrogel solution, preferably a liquid alginate solution, and a, preferably transportable, sample carrier. Layerwise applying (S2) the liquid hydrogel solution onto the sample carrier in a temperature environment, the temperature of which is below the freezing point of the hydrogel solution, to produce a frozen 3D layered hydrogel structure. In order to increase
(Continued)

advantageously the porosity of the 3D layered hydrogel structure, i.e. the proportion of small voids, cavities and/or depressions in the 3D layered hydrogel structure, the method according to the invention further comprises the step of drying (S3) of the frozen 3D layered hydrogel structure, e.g. by means of freeze-drying, to produce a porous 3D hydrogel structure. The invention relates further also to a device for the layerwise building-up of three-dimensional hydrogel structures.

14 Claims, 7 Drawing Sheets

(51) Int. Cl.

| | | |
|---|---|---|
| A61L 27/20 | (2006.01) | |
| A61L 27/22 | (2006.01) | |
| A61L 27/26 | (2006.01) | |
| A61L 27/38 | (2006.01) | |
| A61L 27/52 | (2006.01) | |
| A61L 27/56 | (2006.01) | |
| B29C 64/106 | (2017.01) | |
| B29C 64/209 | (2017.01) | |
| B33Y 10/00 | (2015.01) | |
| B33Y 30/00 | (2015.01) | |
| B33Y 40/20 | (2020.01) | |
| C08L 5/04 | (2006.01) | |
| B29K 105/00 | (2006.01) | |
| B29K 105/16 | (2006.01) | |

(52) U.S. Cl.
CPC .............. *A61L 27/26* (2013.01); *A61L 27/38* (2013.01); *A61L 27/52* (2013.01); *A61L 27/56* (2013.01); *B29C 64/106* (2017.08); *B29C 64/209* (2017.08); *B33Y 10/00* (2014.12); *B33Y 30/00* (2014.12); *B33Y 40/20* (2020.01); *C08L 5/04* (2013.01); *B29K 2005/00* (2013.01); *B29K 2105/0061* (2013.01); *B29K 2105/16* (2013.01)

(58) Field of Classification Search
CPC ... B29C 64/135; B29C 64/255; B29C 64/245; B29C 64/209; B29C 64/364; C08L 5/04; A61L 27/18; A61L 27/20; A61L 27/22; A61L 27/26; A61L 27/38; A61L 27/52; A61L 27/56; B33Y 40/20; B33Y 30/00; B33Y 10/00

See application file for complete search history.

(56) References Cited

U.S. PATENT DOCUMENTS

| | | | |
|---|---|---|---|
| 2015/0289500 A1* | 10/2015 | Fuhr | A01N 1/0257 62/48.2 |
| 2018/0326665 A1* | 11/2018 | Gatenholm | B29C 64/393 |

FOREIGN PATENT DOCUMENTS

| | | | | |
|---|---|---|---|---|
| CN | 107320780 A | | 11/2017 | |
| EP | 1141128 B1 | | 12/2006 | |
| EP | 2679669 A1 | | 1/2014 | |
| WO | 2015066705 A1 | | 5/2015 | |
| WO | WO-2017066727 A1 | * | 4/2017 | .......... B29C 64/106 |
| WO | 2018073235 A1 | | 4/2018 | |
| WO | 2018130949 A1 | | 7/2018 | |

OTHER PUBLICATIONS

Adamkiewicz et al. "Cryogenic 3D printing for tissue engineering." Cryobiology 71.3 (2015): 518-521.
Duan et al. "3D bioprinting of heterogeneous aortic valve conduits with alginate/gelatin hydrogels." Journal of piomedical materials research Part A 101.5 (2013): 1255-1264.
Fischer et al. "3D printing of hydrogels in a temperature controlled environment with high spatial resolution." Current Directions in Biomedical Engineering 2.1 (2016): 109-112.
International Search Report of PCT/EP2019/072999 dated Nov. 12, 2019.
Notification of Reasons for Refusal from corresponding JP 2021-514121 mailed May 10, 2022.
English Abstract for CN 1820791 A (2006).
English Abstract for CN 107041971 A (2017).
English Abstract for CN 107320780 A (2017).

* cited by examiner

METHOD FOR PRODUCING THREE-DIMENSIONAL HYDROGEL STRUCTURES AND DEVICE FOR THE LAYERWISE BUILDING-UP OF SUCH HYDROGEL STRUCTURES

CROSS-REFERENCE TO RELATED APPLICATIONS

This application is a U.S. National Phase Application of PCT/EP2019/072999, filed Aug. 28, 2019, which claims priority to EP 18194428.1, filed Sep. 14, 2018, the contents of which applications are incorporated herein by reference in their entireties for all purposes.

The invention relates to a method for producing three-dimensional, preferably porous, hydrogel structures by means of layer build-up technique. The invention relates further also to a device for the layerwise building-up of three-dimensional hydrogel structures.

Hydrogels are crosslinked, hydrophilic polymer networks, which are able to absorb large quantities of water or other liquids. Because of their biocompatibility, their tissue-like mechanical properties and the easy incorporation of therapeutic active ingredients and/or cells, hydrogels are particularly suitable for the synthetic production of biological tissues, so-called "tissue engineering".

For this, usually scaffold structures of hydrogel are first created, onto which subsequently, or in some cases even already during their production, living cells are applied. In this context, the use of 3D printing technology structures is also known in the prior art, in order to create appropriate hydrogel scaffold for the production of a tissue construction that is as realistic as possible, like for example those required for synthetic transplants. For example the scientific article by B. Fischer et al., "*3D printing of hydrogels in a temperature controlled environment with high spatial resolution*", CDBME, 2, 109 (2016) discloses a layerwise application of an alginate solution by means of a 3D printer at temperatures between −20° C. and −15° C., in order first to create frozen hydrogel scaffold structures, which are subsequently crosslinked by means of gelling and thereby stabilised.

A problematic matter in this connection however is that the scaffold structures must also have an appropriate porosity for the growth, nutrient supply and migration of the cells in the hydrogel structures. To solve this problem, EP 2 679 669 A1 proposes the addition of a further gel additive, preferably gelatine, to the hydrogel solution before the printing procedure. The dispersedly distributed droplets of gelatine prevent the existing space from becoming completely filled up with hydrogel solution and after stabilisation of the hydrogel solution (gelling) can simply be washed out, as a result of which a hydrogel structure with voids or pores emerges. A disadvantage of this method however is the fact that with the use of a mixture of hydrogel and gel additive a homogeneous pore distribution across the entire hydrogel scaffold structure cannot be guaranteed owing to separation processes. Furthermore, during gelling of the hydrogel structures, the diffusion of the gelling solution into the inside is hampered owing to the gelatine particles still present, which can lead to inhomogeneous gelling or the loss of fine structures.

Accordingly an object of the invention is therefore to provide a method for producing three-dimensional, preferably porous, hydrogel structures and also a device, with which the disadvantages of the previous solutions can be avoided. More particularly in this regard it is an object of the invention to provide an easy possibility for creating porous hydrogel structures with controllable and defined pore properties.

These objects are achieved by means of a method and a device of the invention. Advantageous embodiments and applications of the invention are explained in more detail in the description below with partial reference to the figures.

SUMMARY OF THE INVENTION

According to the invention a method for producing three-dimensional, 3D, hydrogel structures by means of layer build-up technique is provided, wherein the method comprises the following steps:

Providing a liquid hydrogel solution, preferably a liquid alginate solution, and a, preferably transportable, sample carrier. The liquid hydrogel solution can be for example 0.3-1.5% aqueous alginate solution, while the sample carrier is made preferably of a thermally conductive material.

The method comprises further layerwise applying the liquid hydrogel solution onto the sample carrier in a temperature environment, the temperature of which is below the freezing point of the hydrogel solution, to produce a frozen 3D layered hydrogel structure. Preferably the layerwise applying takes place in such a way that—as is usual in the layer build-up technique—a new layer is applied onto the previously applied layer, which in the particular case is also already frozen as far as possible. For this the temperature of the temperature environment can be adjusted by way of a cold gas, for example through the feeding-in of cold nitrogen gas into the region of the sample carrier. Alternatively however the adjusting of the temperature can also come about by way of a cold liquid, for example liquid nitrogen, a heat exchanger device and/or a Peltier element device.

In order to increase advantageously the porosity of the 3D layered hydrogel structure, i.e. the proportion of small voids, cavities and/or depressions in the 3D layered hydrogel structure, the method according to the invention further comprises the step of drying of the frozen 3D layered hydrogel structure to produce a porous 3D hydrogel structure. This drying step can take place immediately after the layerwise application, i.e. after the complete 3D layered hydrogel structure has been created; alternatively the drying can also take place already simultaneously with the layerwise application.

The drying can be accomplished by means of freeze-drying. Alternatively infrared (IR) drying or a so-called critical- or supercritical-point drying (CPRD) method can be used for drying. Different drying methods can also be combined, e.g. so that different drying methods are used successively over time.

Critical- or supercritical-point drying is a form of drying, wherein the phase transition of a solvent (e.g. $CO_2$/methanol/acetone) is influenced by pressure and temperature, such that, instead of transitioning from solid to gaseous (freeze-drying) or liquid to gaseous (boiling/simmering), it transitions from liquid to a supercritical fluid and then into a gaseous state. The advantage is that no phase boundaries are crossed and as a result any possible negative effects of drying (e.g. loss of structure) are avoided.

Moreover the drying, e.g. the freeze-drying, which can also be designated as sublimation drying or lyophilisation, can take place in a plurality of stages, i.e. a main drying step and a further drying step at different ambient temperatures and/or ambient pressures. Thus advantageously a dry and thereby storable porous 3D hydrogel structure can be created. In this connection the expression "porous 3D hydrogel structure" is to designate the 3D hydrogel structure that is obtained through the drying step. The porosity of the 3D hydrogel structure offers furthermore the advantage that in this way homogeneous, large-volume structures can also be created, as the gelling agent, in a subsequent gelling of the structures, can also penetrate quickly and evenly into the inside of the 3D hydrogel structures and thus any thawing and running of the structures before the actual stabilising of the structures is prevented through gelling.

In order thereby to achieve advantageously a precise and reproducible production of the 3D layered hydrogel structures, the step of layerwise application by means of a device for the layerwise building-up of three-dimensional hydrogel structures can be performed according to one aspect of the invention. In this connection the device can also be designated as 3D printing device. For this the device can comprise the following features: a print-head for metered release of the liquid hydrogel solution, for example of an aqueous alginate solution, a support to accommodate the sample carrier and a positioning device, which is configured to change a relative position of the print-head to the support in three spatial directions. In this connection the "changing" of the relative position can comprise the movement of the print-head in relation to a fixed support, the movement of the support in relation to a fixed print-head and also the movement of both components relative to each other. Preferably the positioning and/or the dosing of the applied quantity of hydrogel solution, which in this connection can also be designated as printing medium or ink, is controlled by a control device. Furthermore the print-head here can comprise a dosing needle, an extruder die and/or other dosing device and/or a heating device to regulate the temperature of the hydrogel solution.

According to one variant the layerwise application can however also be performed with a hand-operated dosing device, e.g. a pipette.

According to a further aspect of the invention the drying step can comprise sublimating at least a part of frozen water from the frozen 3D layered hydrogel structure at reduced pressure. If the previously liquid hydrogel solution additionally or alternatively also comprises other solvents instead of water, the drying step can additionally or alternatively also comprise sublimation of at least a part of the appropriate frozen solvents from the frozen 3D layered hydrogel structure at reduced pressure. Here the expression "reduced pressure" can designate more particularly a low pressure below standard pressure, i.e. below 1013 mbar, preferably a rough vacuum or fine vacuum. Preferably the frozen 3D layered hydrogel structure is kept in the frozen state and/or at a temperature below room temperature during sublimation. Advantageously gentle drying of the 3D layered hydrogel structure, in which its shape and structure are for the most part retained, is achieved in this way. Additionally or alternatively the drying can be accomplished by means of infrared drying, critical-point drying, and/or supercritical-point drying.

According to a further aspect of the invention a first pore property, for example a pore distribution, of the 3D hydrogel structure can be adjusted in the step of layerwise application by means of at least one first operating parameter. Additionally or alternatively a second pore property, for example a mean pore size, of the 3D hydrogel structure can be adjusted in the drying step by means of at least one second operating parameter. In other words a desired first and/or second pore property can be adjusted as a function of the first and/or second operating parameter, or the first and/or second operating parameter can be selected particularly, so as to achieve a certain first and/or second pore property. To this end the method can, for example, comprise the step: setting of a value of the first operating parameter as a function of the first pore property, preferably using a previously determined characteristic curves and/or setting of a value of the second operating parameter as a function of the second pore property, preferably using a previously determined characteristic curve. The first and second pore properties can be either different or the same pore properties. For example the pore property porosity of the 3D hydrogel structure can be increased through a reduction in the concentration of the aqueous hydrogel solution in the step of layerwise application as a result of the associated increase in ice crystal formation. Moreover both in the step of layerwise application and also in the drying step, in each case, a plurality of pore properties, e.g. a pore distribution and a mean pore size, can be adjusted. Preferably the first and/or second pore property can also be adjusted variably in the process according to location. The influence of an appropriate parameter on the pore properties can be determined in this connection by means of appropriate preliminary experiments or test series, in which the parameters are varied in a certain value range and the resulting influence on the pore property is observed. This correlation of dependencies can moreover also be stored in the form of characteristic curves. Advantageously 3D hydrogel structures with defined pore properties can thus be created specifically, and through local variation of the pore properties more particularly tissue transitions and/or pathological changes, e.g. scars, can be replicated.

According to a further development of this aspect the first and/or second pore property of the 3D hydrogel structure can be a pore distribution, a porosity, a mean pore size, a mean pore orientation, a mean pore shape and/or a mean pore volume. For example the first and/or second pore property can indeed also be a specific surface and/or some other, not explicitly named, preferably statistical, quantity for characterisation of a pore property without departing from the scope of the invention. Because the aforementioned quantities contribute to the determination of key physical properties of the 3D hydrogel structures, like for example the elasticity, it is possible to achieve advantageously a reliable control of the properties of the hydrogel structure through specific adjustment of these quantities. Accordingly tissue constructions that are as realistic as possible can be created in this way.

According to a further aspect of the invention the at least one first operating parameter can comprise the temperature of the temperature environment, a temperature distribution and/or temperature gradient of the temperature environment, a composition of an atmosphere, in which the liquid hydrogel solution is applied onto the sample carrier (e.g. a mixture of liquid nitrogen and dry ice), a concentration of the liquid hydrogel solution, a viscosity of the liquid hydrogel solution and/or a speed of the layerwise application. For example, by lowering the concentration of the liquid hydrogel solution, it is possible to achieve an increase in porosity. In this connection preferably—more particularly with correlating quantities such as temperature and viscosity—a plurality of these operating parameters is taken into account in the adjustment of the first pore property of the 3D hydrogel structure. Because the aforementioned operating parameters are moreover easy to monitor and/or vary, this advantageously makes reliable and easy production of 3D hydrogel structures with defined pore properties possible.

According to a further aspect of the invention the at least second operating parameter can comprise an ambient temperature, an ambient pressure and/or a duration of the drying procedure. The quantities ambient temperature and ambient pressure can here be understood as the local temperature and pressure on the sample carrier during the drying step. Moreover in the case of simultaneous layerwise application and drying the ambient temperature can be identical with the quantity designated as "temperature of the temperature environment" in the step of layerwise application. Preferably a plurality of the just mentioned operating parameters is also taken into account in the adjustment of the second pore property of the 3D hydrogel structure. Here also the easy monitoring and/or varying of the operating parameters advantageously makes reliable and easy production of 3D hydrogel structures with defined pore properties possible.

If the method according to the invention is performed with a 3D printing device as described above, according to a further aspect of the invention the at least one first operating parameter can comprise a spacing between the print-head and the sample carrier and/or a spacing between the print-head and the last applied layer of hydrogel solution. Preferably this is a, particularly preferably regulated, spacing in relation to the topmost layer during the application of a new layer of the liquid hydrogel solution. In this connection it was established on the part of the inventor that the porosity of the hydrogel structures can be increased by enlarging the spacing between print-head and the last applied layer of hydrogel structures. Thus again 3D hydrogel structures with defined pore properties can advantageously be created easily and reliably.

According to a further aspect of the invention the method can comprise the step of mechanical structuring of the porous 3D hydrogel structure. In other words, the porous 3D hydrogel structure can be further mechanically processed after the drying step. For example, channels can be melted and/or drilled into the porous 3D hydrogel structure, in order, for example, advantageously to model blood vessels in the 3D hydrogel structures. In this connection it is also possible to speak of a vascularisation of the porous 3D hydrogel structure. Furthermore the surface of the porous 3D hydrogel structure can be roughened and/or ground. Also, for example, defined shapes can be pressed into the porous 3D hydrogel structure by means of stamps and/or defined shapes can be punched out of the porous 3D hydrogel structure. Advantageously, through mechanical structuring, the local properties of the 3D hydrogel structures can be varied even further and thus tissue models that are as realistic as possible can be created.

According to a further aspect of the invention the method can comprise the step of storing of the porous 3D hydrogel structure in a dry environment. Preferably, in this connection, the environment has a low atmospheric humidity and/or is in contact with a drying agent, for example silica gel. Alternatively or in addition the storage can be performed in a protective gas atmosphere, e.g. with nitrogen or an oxygen-free atmosphere, in order to prevent oxidation. As a result of the earlier drying of the 3D layered hydrogel structures these can thus be kept advantageously over a long period, during which physical and/or chemical changes, e.g. hydrolysis, which would otherwise take place under the humid conditions, can possibly be suppressed.

Additionally or alternatively the method can also comprise the step of storing of the porous 3D hydrogel structure in a cryogenic environment. Thereby the cryogenic environment has preferably a temperature below −100° C., particular preferably below −120° C. Additionally or alternatively the method can also comprise the moistening of the porous 3D hydrogel structure with a liquid, preferably with water and/or with other solvents. Preferably this step takes place immediately after a just described storage of the porous 3D hydrogel structures. In this connection it is thus possible to speak also of a rehydration of the porous 3D hydrogel structures. As a result of the moistening of the porous 3D hydrogel structures humid conditions can advantageously again be provided for a subsequent coating with cells and/or proteins.

According to a further aspect of the invention the method can comprise the step of gelling of the porous 3D hydrogel structure through chemical crosslinking by means of multivalent cations, preferably $Ba^{2+}$, $Mg^{2+}$, $Ca^{2+}$, $Fe^{2+}$ and/or $Sr^{2+}$. For this, preferably, the porous 3D hydrogel structure is incubated in a bath of gelling solution, e.g. $BaCl_2$ solution. Particularly preferably the step of gelling of the porous 3D hydrogel structure takes place after the step of drying of the frozen 3D layered hydrogel structure. Advantageously, as a result of this, the gelling agent can also penetrate quickly and evenly into the inside of the 3D hydrogel structures. Alternatively the drying step can also take place after the gelling of the porous 3D hydrogel structure or the method can comprise a further gel drying step, i.e. the further step of drying of the gelled 3D hydrogel structure by means of freeze-drying. Advantageously the shelf life of the gelled 3D hydrogel structures is again increased in this way.

Additionally or alternatively the method can also comprise the step of coating of the porous 3D hydrogel structure with proteins, preferably proteins from an extracellular matrix, and/or cells, preferably human cells. Here the term "extracellular matrix" is intended to designate the entirety of all macromolecules in the intercellular space. In simplified terms, it can be composed of the structural components of a tissue which are located outside the cells. In this connection it is also possible to speak of an activation or functionalisation of the porous 3D hydrogel structures. Moreover the porous 3D hydrogel structure can be incubated with a cell culture solution. Advantageously patient- and/or illness-specific tissue models can be created in this way, so for example new medications can be tried out on them.

In addition to or instead of a later functionalisation of the 3D hydrogel structures various additives can be added to the hydrogel solution already before the actual printing. Because the printing substance used is thus no longer a pure hydrogel solution, in this connection the expression "hybrid ink" can also be used for the substance used for layerwise application. Here the liquid hydrogel solution can contain at least one of the following additives:

porogens, i.e. pore-forming and promoting substances (cf. also EP 114 11 28 B1), e.g. salts. Porogens are thus substances with which one can create or widen pores specifically, e.g. salt crystals such as NaCl crystals,
surfactants—these can influence the drying and also the formation of pores (e.g. Pluronic or Tween),
polyethylene glycol,
a protein, preferably a protein from an extracellular matrix,
cells, preferably human cells,
collagen,
gelatine,
bulking agents—these have a stabilising effect on the scaffold structure during drying (e.g. PEG, saccharides etc . . . ,),
an aqueous solution, preferably a solution of sugar and/or common salt, and/or
a gelling agent for chemical crosslinking by means of multivalent cations.

In this way, advantageously, a more homogeneous distribution of the various additives in the hydrogel structures can be achieved than is possible with later coating by way of diffusion processes. For example, here, a part of the later gelling agent, e.g. $BaCl_2$, can be integrated into the construct during application and in this way act "from the inside out" and thus also in places that are difficult to access from outside. Furthermore the porous 3D hydrogel structures can be devised even more specifically, with for example a non-gellable solution, e.g. solution of sugar and/or common salt, being added to the hydrogel solution, in order thereby specifically to create voids or channels for a vascular system. Additionally or alternatively to the "addition" of the aforementioned substances to the hydrogel solution the method can also comprise the step of the application of one or more of the above substances in pure form, i.e. without the combination with liquid hydrogel solution.

According to a further aspect of the invention the liquid hydrogel solution can contain a first additive, which gels by means of chemically induced crosslinking, preferably collagen, and a second additive, which gels by means of thermally induced crosslinking, preferably gelatine. In other words, the applied medium or hybrid ink comprises substances with three different gelling types (ions, chemically and thermally induced). In this connection a subsequent gelling of the three substances can take place simultaneously, partly simultaneously or sequentially. Advantageously the local properties of the 3D hydrogel structures can, as a result of this, again be varied even further or devised more specifically and in this way tissue models that are as realistic as possible can be created.

Advantageous embodiments of the device for the layerwise building-up of three-dimensional hydrogel structures, which can also be designated as 3D printing device, are described below. As has already been described above, said device comprises a print-head for metered release of a liquid material, preferably a liquid hydrogel solution, a support to accommodate the sample carrier and a positioning device, which is configured to change a relative position of the print-head to the support in three spatial directions. In this connection the "changing" of the relative position can comprise the movement of the print-head in relation to a fixed support, the movement of the support in relation to a fixed print-head and also the movement of both components relative to each other. According to a further aspect the 3D printing device can additionally have a heat-insulating tray, into which a cold gas, preferably nitrogen, is fed. In other words the heat-insulating tray can be configured for a cold gas, preferably nitrogen, to be fed into. Alternatively, however, cold liquids, for example liquid nitrogen, can also be fed into the heat-insulating tray. In a simple manner an appropriately cold temperature environment can thus be created for performing the method. Furthermore the support to accommodate a sample carrier can be disposed inside the heat-insulating tray and be configured as grid-like support. Advantageously this firstly provides a good mechanical hold for the sample carrier and secondly hampers as little as possible the movements of the refrigerating agent flowing through the heat-insulating tray.

Advantageously this device is particularly suited for performing the afore-described method step of layerwise application of the liquid hydrogel solution, wherein the here disclosed device can moreover also have all the features, as they have been described already in the course of the method in this document, and vice versa. That means that the features of the method disclosed in accordance with the method are therefore to be disclosed and claimable also in connection with the device and the features of the device disclosed in accordance with the device are therefore to be disclosed and claimable also in connection with the method. Furthermore the 3D printing device is however also to be disclosed and claimable independently of the method as subject-matter per se.

According to a further aspect the print-head of the device can comprise a dosing needle, which is surrounded by a hydrophobic material and/or hydrophobic coating and/or Parafilm and/or Nescofilm in order to prevent drop formation. Alternatively another flexible, hydrophobic material, preferably made of paraffin wax and polyethylene, can also be used. Advantageously drop formation on the dosing needle is thereby prevented as far as possible.

Additionally or alternatively the heat-insulating tray can also be built up of two layers, wherein the first layer has a lower thermal conductivity than the second layer. In this connection an open-top container with high walls and a flat bottom can be understood to be a tray. Here, preferably, the layer lying further to the outside, which in this connection can be designated as first layer, has a lower thermal conductivity than the layer lying further to the inside. Preferably the second layer is in contact with the support to accommodate the sample carrier. Advantageously it is thus possible to achieve sufficient thermal insulation in relation to the environment together with simultaneous effective cooling of the accommodating means and thus of the sample carrier.

Additionally or alternatively the temperature of the cold gas that is fed in can be adjusted variably. Preferably the temperature can be adjusted and/or regulated to a certain value. Particularly preferably the temperature of the gas that is fed in, for example nitrogen, can be adjusted in a range between $-180°$ C. and $25°$ C. by means of a cold-gas device. Alternatively the temperature of a liquid that is fed in, a heat exchanger device and/or a Peltier element device can also be adjusted variably. Advantageously, through the simple varying of the temperature, the resulting pore properties of the 3D hydrogel structures can be adjusted specifically.

Additionally or alternatively the sample carrier can be made of glass. Moreover the sample carrier can comprise a film, a membrane and/or a porous material. Preferably the sample carrier has an essentially rectangular shape. Advantageously sufficient thermal coupling between sample carrier and hydrogel structure can be achieved in this way, while at the same time easy detachment of the hydrogel structures from the sample carrier is possible.

BRIEF DESCRIPTION OF THE DRAWINGS

The afore-described aspects and features of the invention can be combined with one another at will. Further details and advantages of the invention are described below with reference to the attached drawings. The figures show the following.

DETAILED DESCRIPTION OF PREFERRED EMBODIMENTS

Figure 1:
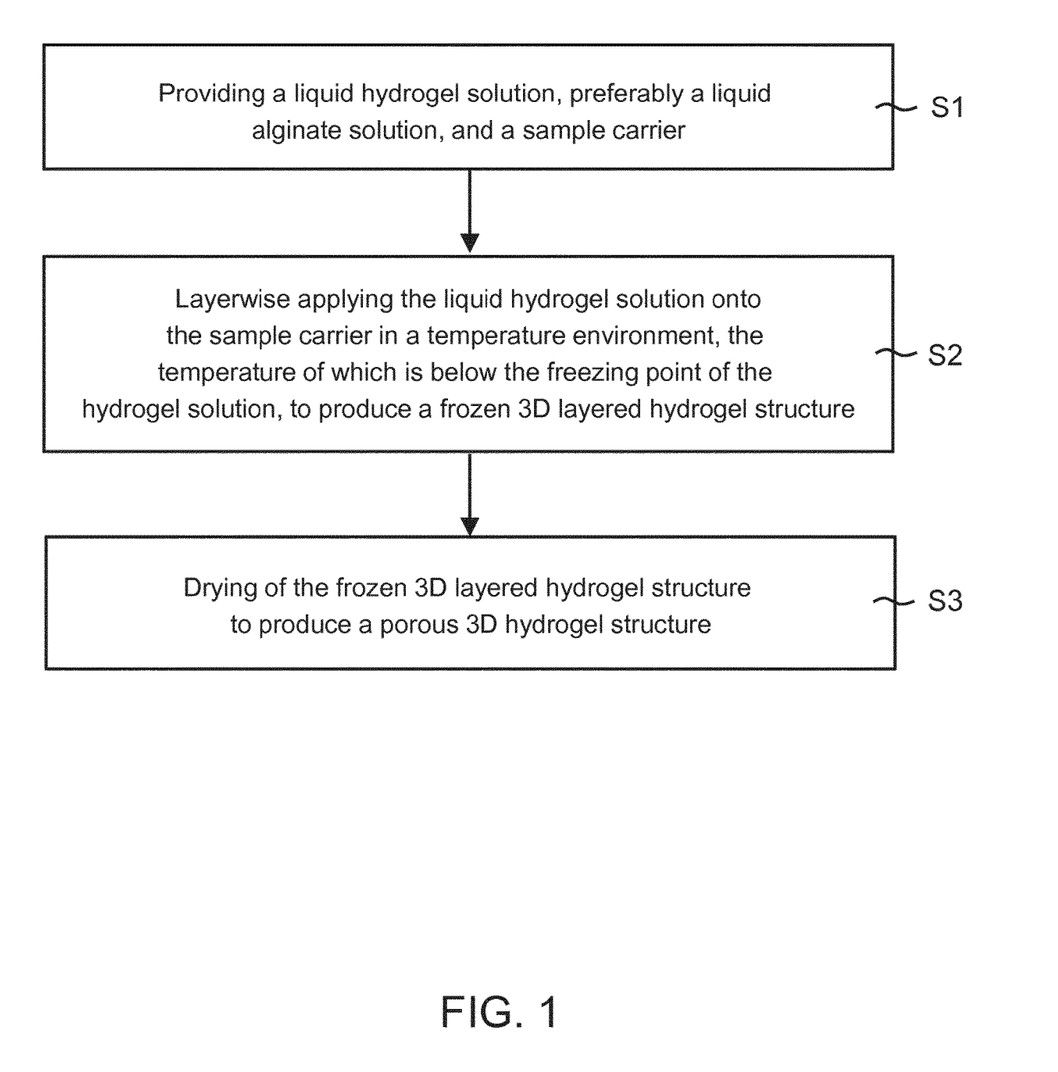
FIG. 1: a flow chart of the method for producing 3D hydrogel structures by means of layer build-up technique according to an embodiment of the invention.

FIG. 1 shows a flow chart of the method for producing 3D hydrogel structures by means of layer build-up technique according to an embodiment of the invention. To this end, in step S1, a liquid hydrogel solution, for example 0.3-1.5% aqueous alginate solution, and a, preferably transportable, sample carrier 4 are provided. The term "alginate" denotes unbranched anionic polysaccharide chains, which are obtained primarily from brown algae. In step S2 the liquid hydrogel solution is then applied layerwise onto the sample carrier 4 in a temperature environment, the temperature of which is below the freezing point of the hydrogel solution, to produce a frozen 3D layered hydrogel structure 1$a$. For this, usual aqueous hydrogel solutions have for example a freezing point in the range between $-10°$ C. and $0°$ C., in respect of which the freezing point of a liquid hydrogel solution can also be determined experimentally by simple cooling and observation of the temperature of the phase transition from liquid to solid. Preferably the layerwise application takes place by means of a device 10 for the layerwise building-up of three-dimensional hydrogel structures, as described in this document. In step S3 the frozen 3D layered hydrogel structure 1$a$ is then dried to produce a porous 3D hydrogel structure 1$b$. The drying step can be performed, for example, by means of freeze-drying, which can also be designated as sublimation drying or lyophilisation. To this end at least a part of the frozen solvent, for example water, can be sublimated from the frozen 3D layered hydrogel structure 1$a$ at reduced pressure, i.e. at a pressure below 1013 mbar. Advantageously the porosity of the 3D layered hydrogel structure, i.e. the proportion of small voids, cavities and/or depressions in the 3D layered hydrogel structure, can thus be increased and additionally the shelf life of the structures produced can be improved. Additionally or alternatively the drying can be accomplished by means of infrared drying, critical-point drying, and/or supercritical-point drying.

Figure 2:
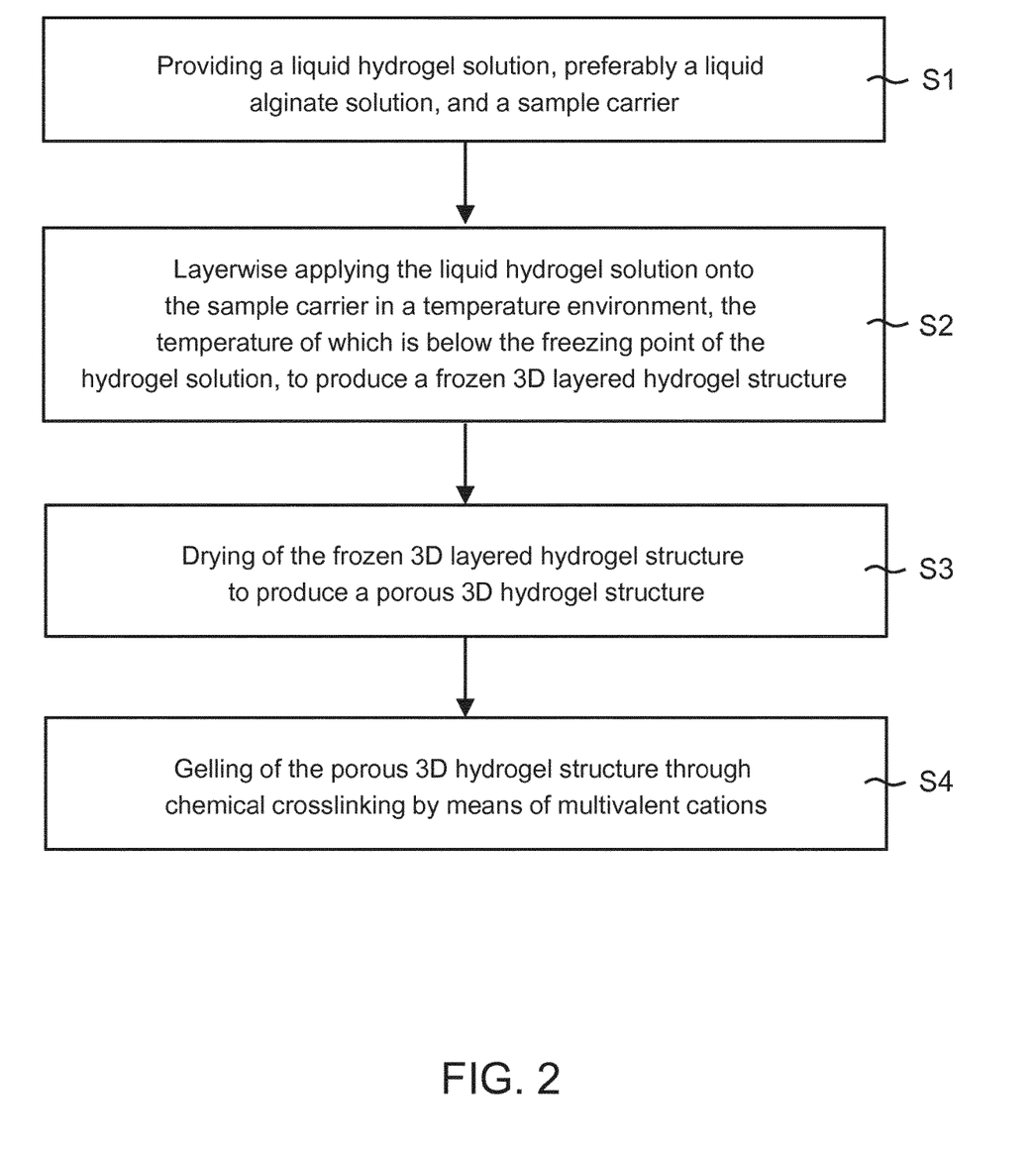
FIG. 2: a flow chart of the method according to a further embodiment of the invention.

FIG. 2 shows a flow chart of the method according to a further embodiment of the invention. In contrast to the embodiment shown in FIG. 1 the method comprises the additional step S4, in which the porous 3D hydrogel structure 1$b$ is gelled by chemical crosslinking by means of multivalent cations, e.g. $Ba^{2+}$, $Mg^{2+}$, $Ca^{2+}$, $Fe^{2+}$ and/or $Sr^{2+}$. In this procedure—designated also as ionic gelling—the multivalent cations are deposited between the polymer chains, as a result of which an association of the polymer chains and thereby the formation of a linked polymer network is induced by way of electrostatic interactions. In other words, the 3D hydrogel structure becomes dimensionally stable. To this end the porous 3D hydrogel structure 1$b$ is preferably incubated in a bath of gelling solution, e.g. $BaCl_2$ solution. Preferably this can take place in the still frozen state of the 3D hydrogel structure. As a result of this, advantageously, dimensionally stable scaffold structures of hydrogel, onto which living cells can subsequently be applied for the production of tissue models, are obtained.

Figure 3:
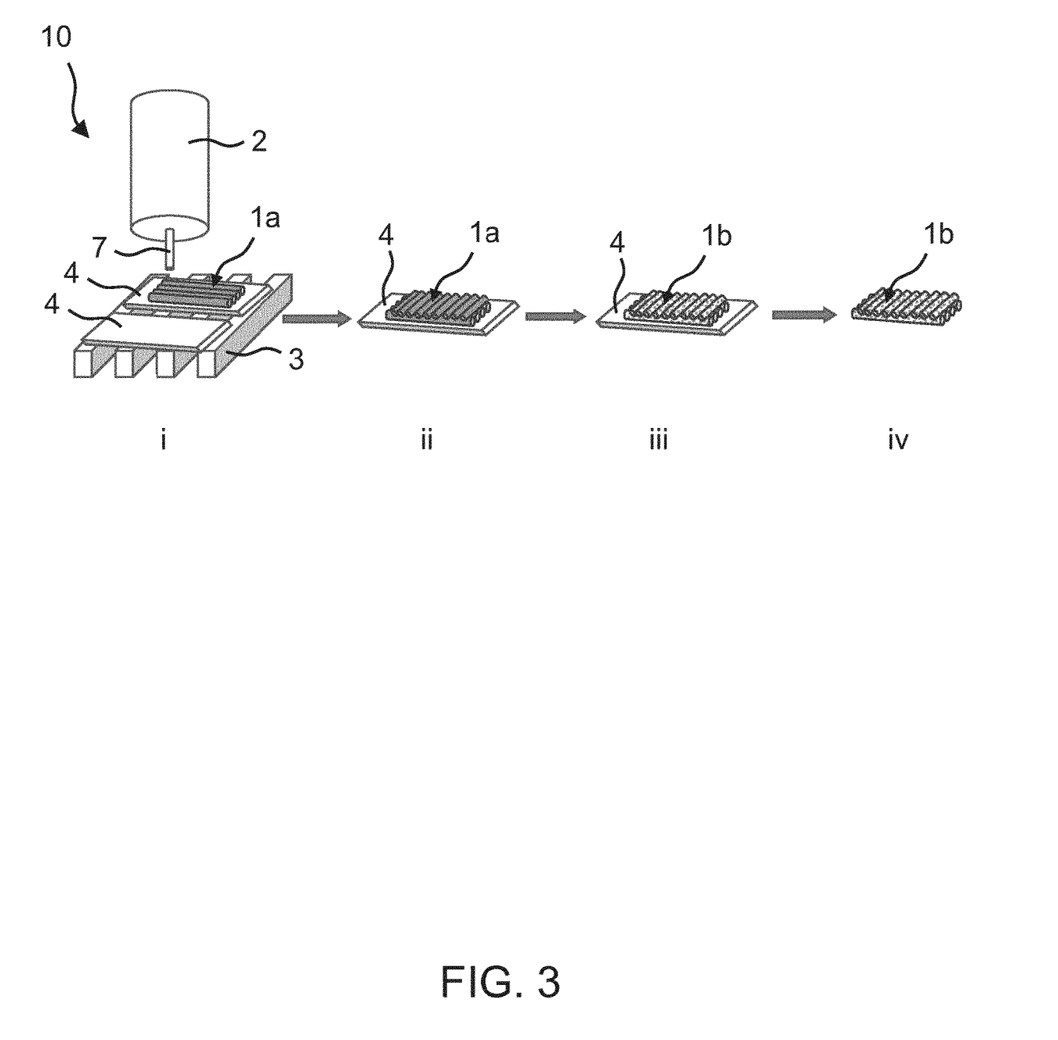
FIG. 3: a schematic representation of selected method steps according to a further embodiment of the invention.

FIG. 3 shows a schematic representation of selected method steps according to a further embodiment of the invention. After a liquid hydrogel solution, not described in any further detail, and a transportable sample carrier 4 in the form of a glass slide have been provided, step i shows schematically the layerwise application of the liquid hydrogel solution onto the sample carrier 4 in a temperature environment, the temperature of which is below the freezing point of the hydrogel solution, and thus corresponds to the preceding method step S2. For layerwise application, in the present case, a device 10 for the layerwise building-up of three-dimensional hydrogel structures is used. This comprises a print-head 2 for metered release of the liquid hydrogel solution by way of a dosing needle 7, a grid-like support 3 to accommodate the sample carrier 4 and a positioning device 5 (not represented), which is configured to change a relative position of the print-head 2 to the support 3 in three spatial directions. In this connection the support 3 and the sample carrier 4 can be so dimensioned, that—as shown here—a plurality of sample carriers 4 can be positioned on the support 3. Step ii shows the transportable sample carrier 4 taken from the 3D printing device with the frozen 3D layered hydrogel structure 1$a$ located thereupon. The sample carrier 4 can now be transferred for example into a freeze-drying or any other drying type apparatus, in which the next method step of drying now takes place, while simultaneously a further frozen 3D layered hydrogel structure 1$a$ is produced in the 3D printing device. Step iii shows a porous 3D hydrogel structure 1$b$ produced, by drying of the frozen 3D layered hydrogel structure 1$a$, e.g. by means of freeze-drying, and corresponds thereby to method step S3. During the drying procedure at least a part of the contained solvent or water is removed from the frozen 3D layered hydrogel structure 1$a$, e.g. through sublimation. If freeze-drying is used the ambient pressure surrounding the frozen 3D layered hydrogel structure 1$a$ can be lowered, preferably with adjustment to a pressure range of a few mbar or less. Advantageously, as a result of this, gentle drying of the frozen 3D layered hydrogel structure 1$a$ is achieved, during which its shape and structure are for the most part retained. Step iv shows the porous 3D hydrogel structure 1$b$, detached from the sample carrier 4, which can now subsequently be gelled, mechanically structured and/or stored.

Figure 4:
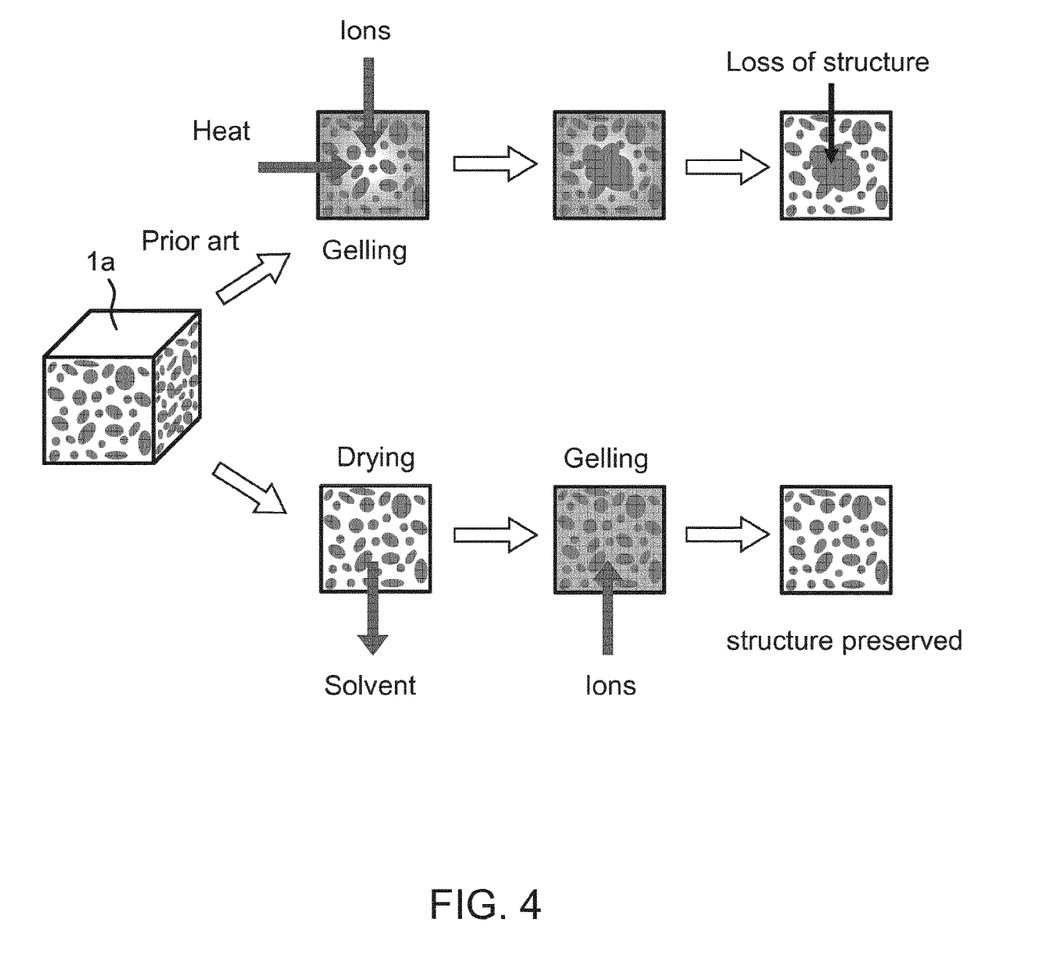
FIG. 4: a comparison of the schematically represented morphology of the 3D hydrogel structures according to a method known to date in the prior art (top) and an embodiment of the invention (bottom)

FIG. 4 clarifies the advantages arising from the method according to the invention in respect of the production of dimensionally stable, i.e. gelled, porous 3D hydrogel structures 1$b$ in comparison with the methods known in the prior art. The starting point here is the frozen 3D layered hydrogel structure 1$a$ produced preferably by means of layer build-up technique. If the frozen 3D layered hydrogel structure 1$a$, as shown in the above representation, is gelled immediately according to the methods known in the prior art, the gelling solution is able to penetrate or diffuse only slowly into the inside of the 3D layered hydrogel structure on account of the solvent present in the structure. Accordingly, frozen regions are able to thaw, before they have been stabilised by gelling. The consequence is a loss of structure in these regions, as illustrated schematically in the top right image. This problem can be avoided to a large extent by means of the drying step, as shown in the lower representations. Here the frozen 3D layered hydrogel structure 1$a$ is first dried, e.g. by means of freeze-drying, during which the solvent present in the structure escapes. In the gelling that follows the gelling agent, e.g. $BaCl_2$, can penetrate the structure homogeneously and as far as possible unhindered. As a result of this even fine pore structures in the inside are retained, as is represented in the bottom right image.

Figure 5:
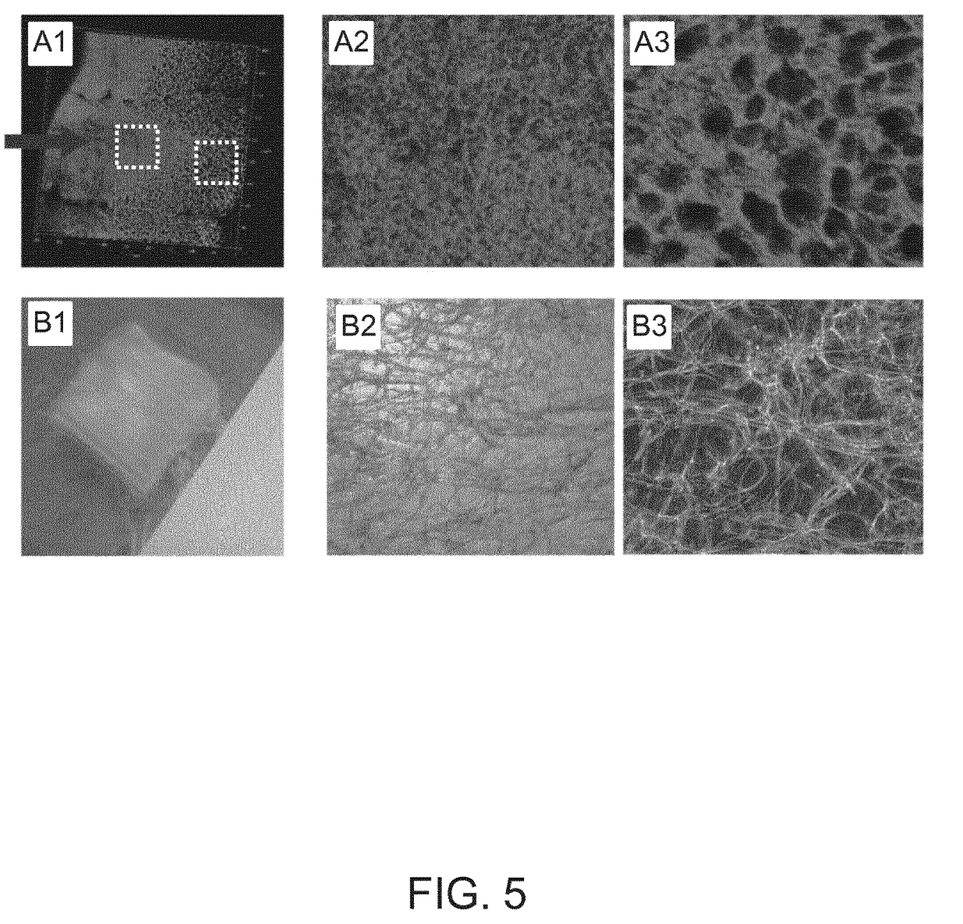
FIG. 5: a comparison of photographs and micrographs of 3D hydrogel structures produced according to a method known to date in the prior art (top) and an embodiment of the invention (bottom)

FIG. 5 shows a comparison of photographs and micrographs of real 3D hydrogel structures, produced according to a method known to date in the prior art (top) and an embodiment of the invention (bottom). Here image A1 shows a hydrogel structure which was prepared by means of 3D pressure followed by gelling, i.e. with a method as known in the prior art. In this connection the arrow points out a previously mentioned loss of structure due to too fast a thawing procedure, said loss of structure being represented, enlarged, in image A2. In the porous structure no longer present in this region on account of the liquefying and associated compression by the melting process any growth of cells here is hardly possible. In contrast, image A3 shows regions of the same sample in which a sufficiently high (desired) porosity is still present. In order to achieve a homogeneous hydrogel structure throughout, the method according to the invention comprises an additional gel drying step. A corresponding 3D hydrogel structure produced by means of 3D printing, then dried (here: freeze dried) and gelled, is shown in image B1. As can be seen, magnified four times (B2) and ten times (B3), the sample has a sufficiently high porosity across the whole structure, without any compressed regions appearing.

Figure 6:
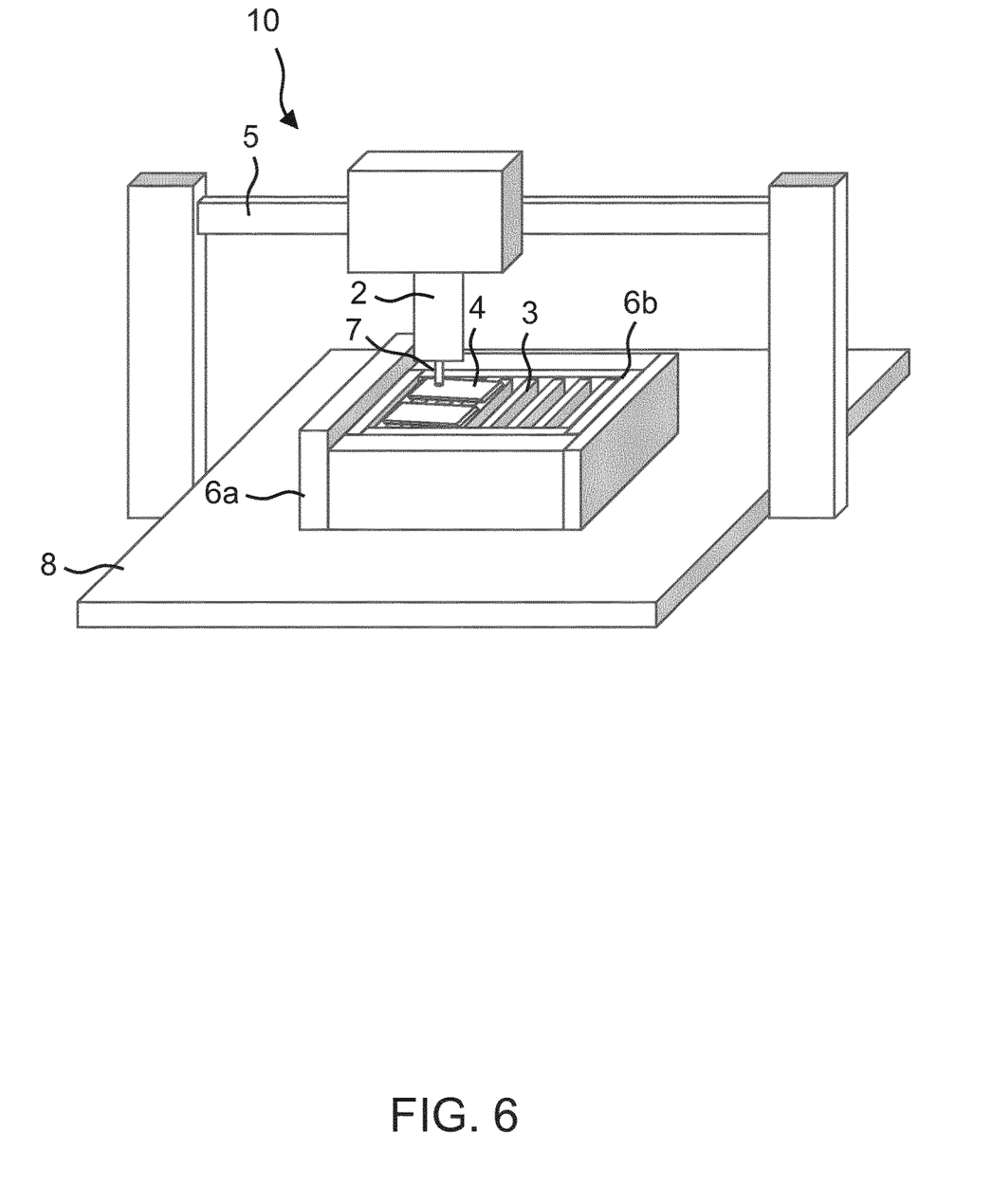
FIG. 6: a schematic representation of a device for the layerwise building-up of three-dimensional hydrogel structures according to an embodiment of the invention.

FIG. 6 shows a schematic representation of a device 10 for the layerwise building-up of three-dimensional hydrogel structures according to an embodiment of the invention. In this connection the device 10, also designated as 3D printing device, comprises a print-head 2 with a heatable dosing needle 7 for metered release of a liquid material, preferably a liquid hydrogel solution. To this end the liquid material can for example be pushed out of the heatable dosing needle 7 by means of air pressure. Moreover the device 10 comprises a heat-insulating tray 6, into which a cold gas, for example cold nitrogen gas at −50° C., is fed. Particularly preferably the temperature of the cold gas that is fed in can be adjusted variably. For this the heat-insulating tray 6 can be located on a plate 8, which is orientated as horizontally as possible. Furthermore the device 10 comprises a grid-like support 3, disposed inside the heat-insulating tray 6, to accommodate a sample carrier 4 and also a positioning device 5, which is configured to change a relative position of the print-head 2 to the support 3 in three spatial directions. In the present case the positioning device 5 is embodied as portal-like structure with a guide mechanism which makes possible a relative movement of the print-head 2 to the fixed support 3 or to the fixed sample carrier 4. In this connection, for producing a frozen 3D layered hydrogel structure, a new layer of the material, preferably hydrogel solution, can be applied in each case onto a previously applied and, as far as possible, already frozen layer by means of appropriate control of the positioning device 5 by way of a control device, which is not represented in any more detail.

Figure 7:
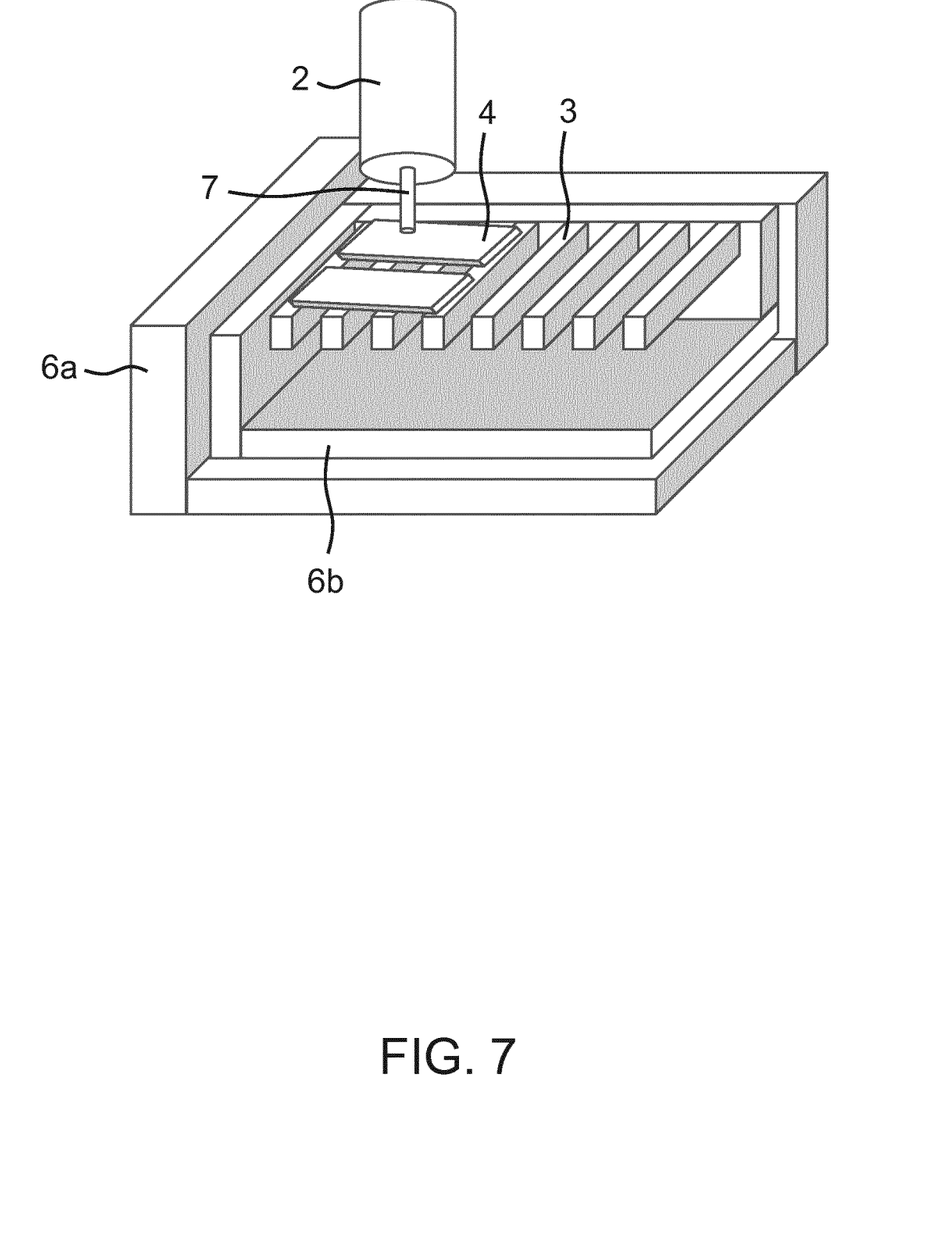
FIG. 7: a detail representation of a section of the device shown in FIG. 6.

FIG. 7 shows a detail representation of a section of the device 10 shown in FIG. 6. Reference should be made here especially to the grid-like support 3 and also the heat-insulating tray 6. In this connection the latter is built up of two layers 6a, 6b—an inner one and an outer one—each layer 6a, 6b forming a hollow block open on one side, in the present case at the top. The layer 6a, lying further to the outside, has a lower thermal conductivity than the layer 6b, lying further to the inside. In other words, the outer layer 6a conducts heat more poorly than the inner layer 6b, i.e. it insulates heat better than the inner layer 6b. Moreover each of the two layers 6a, 6b here, by way of example, has a different thickness, though the two layers 6a, 6b can also have the same thickness without departing from the scope of the invention. Fastened to the inner layer 6b there is also the grid-like support 3 to accommodate the sample carrier 4. In the present case this self-supporting structure comprises a plurality of support bars with a rectangular profile, which are disposed in parallel. Just like the inner layer 6b of the heat-insulating tray 6, the respective support bars are also made of a material that conducts heat as well as possible, in order to guarantee that the sample carrier 4 lying thereupon has a sufficient connection to heat. The grid-like structure of the support 3 firstly offers a good mechanical hold for the sample carrier 4 and secondly hampers as little as possible the movements of the cold gas flowing through the heat-insulating tray 6. At the same time the outer layer 6a ensures the best possible thermal insulation of the interior space from the environment.

Although the invention has been described with reference to certain exemplary embodiments, it is evident to a person skilled in the art that various changes can be implemented and equivalents can be used as substitute without departing from the scope of the invention. Consequently the invention is not to be limited to the disclosed exemplary embodiments, but is to comprise all exemplary embodiments falling within the scope of the attached patent claims. More particularly the invention also claims protection for the subject-matter and the features of the dependent claims independently of the referenced claims.

The invention claimed is:

1. A method for producing three-dimensional, 3D, hydrogel structures by use of a layer build-up technique comprising the steps:
    providing a liquid hydrogel solution and a sample carrier;
    layerwise applying the liquid hydrogel solution onto the sample carrier in a temperature environment, a temperature of which is below a freezing point of the liquid hydrogel solution, to produce a frozen 3D layered hydrogel structure;
    drying of the frozen 3D layered hydrogel structure to produce a porous 3D hydrogel structure; and
    mechanical structuring of the porous 3D hydrogel structure.

2. The method according to claim 1, wherein the layerwise application step is performed with a device for a layerwise building-up of three-dimensional hydrogel structures, comprising:
    a print-head for metered release of the liquid hydrogel solution;
    a support to accommodate the sample carrier; and
    a positioning device, which is configured to change a relative position of the print-head to the support in three spatial directions.

3. The method according to claim 1, wherein
    a) the drying step is performed by freeze-drying and/or sublimating of at least a part of frozen water from the frozen 3D layered hydrogel structure at reduced pressure; and/or
    b) the drying step is performed by infrared (IR) drying or a critical-point drying method.

4. The method according to claim 2, wherein
    a) in the layerwise application step a first pore property of the 3D hydrogel structure is adjusted by at least one first operating parameter; and/or
    b) in the drying step a second pore property of the 3D hydrogel structure is adjusted by at least one second operating parameter.

5. The method according to claim 4, wherein the first and/or second pore property of the 3D hydrogel structure is
    a) a pore distribution;
    b) a porosity;
    c) a mean pore size;
    d) a mean pore orientation;
    e) a mean pore shape; and/or
    f) a mean pore volume.

6. The method according to claim 5, wherein the at least one first operating parameter comprises
   a) the temperature of the temperature environment;
   b) a temperature distribution and/or temperature gradient of the temperature environment;
   c) a composition of an atmosphere, in which the liquid hydrogel solution is applied onto the sample carrier;
   d) a concentration of the liquid hydrogel solution;
   e) a viscosity of the liquid hydrogel solution and/or
   f) a speed of the layerwise application.

7. The method according to claim 5, wherein the at least second operating parameter comprises
   a) an ambient temperature;
   b) an ambient pressure; and/or
   c) a duration of the drying procedure.

8. The method according to claim 5, wherein the at least one first operating parameter comprises a spacing between the print-head and the sample carrier and/or a spacing between the print-head and the last applied layer of hydrogel solution.

9. The method according to claim 1, further comprising at least one of the steps:
   storing of the porous 3D hydrogel structure in a dry environment and/or a protective gas atmosphere;
   storing of the porous 3D hydrogel structure in a cryogenic environment; and/or
   moistening of the porous 3D hydrogel structure with a liquid.

10. The method according to claim 1, further comprising at least one of the steps:
    gelling of the porous 3D hydrogel structure through chemical crosslinking by way of multivalent cations; and/or
    coating of the porous 3D hydrogel structure with proteins and/or cells.

11. The method according to claim 1, wherein the liquid hydrogel solution contains at least one of the following additives:
    porogens to influence pore formation,
    bulking agents,
    surfactants,
    polyethylene glycol,
    a protein,
    cells,
    collagen and/or gelatin,
    an aqueous solution, and/or
    a gelling agent for chemical crosslinking by way of multivalent cations.

12. The method according to claim 1, wherein the liquid hydrogel solution contains a first additive, which gels by chemically induced crosslinking, and a second additive, which gels by thermally induced crosslinking.

13. The method according to claim 1, wherein the liquid hydrogel solution is a liquid alginate solution.

14. The method according to claim 1, wherein the mechanical structuring step comprises at least one of the following steps:
    a) channels are melted and/or drilled into the porous 3D hydrogel structure and/or
    b) the surface of the porous 3D hydrogel structure is roughened and/or ground and/or
    c) defined shapes are pressed into the porous 3D hydrogel structure by means of stamps.

* * * * *